(12) United States Patent
Horie

(10) Patent No.: US 12,239,440 B2
(45) Date of Patent: Mar. 4, 2025

(54) PROBE AND PULSE PHOTOMETRY SYSTEM

(71) Applicant: NIHON KOHDEN CORPORATION, Tokyo (JP)

(72) Inventor: Katsuyuki Horie, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 591 days.

(21) Appl. No.: 17/462,427

(22) Filed: Aug. 31, 2021

(65) Prior Publication Data

US 2022/0071515 A1 Mar. 10, 2022

(30) Foreign Application Priority Data

Sep. 9, 2020 (JP) ................................. 2020-151260

(51) Int. Cl.
*A61B 5/1455* (2006.01)
*A61B 5/00* (2006.01)
*A61B 5/024* (2006.01)

(52) U.S. Cl.
CPC ........ *A61B 5/1455* (2013.01); *A61B 5/02427* (2013.01); *A61B 5/7278* (2013.01);
(Continued)

(58) Field of Classification Search
CPC .............. A61B 5/1455; A61B 5/14551; A61B 5/14552; A61B 5/14553; A61B 5/14532;
(Continued)

(56) References Cited

U.S. PATENT DOCUMENTS 5,810,723 A * 9/1998 Aldrich .............. A61B 5/14551
600/322
6,526,301 B2 2/2003 Larsen et al.
(Continued)

FOREIGN PATENT DOCUMENTS

EP 1 322 216 A1 7/2003
JP 2004-290544 A 10/2004
(Continued)

OTHER PUBLICATIONS

Search Report issued Feb. 8, 2022 by the European Patent Office in counterpart European Patent Application No. 21194526.6.
(Continued)

*Primary Examiner* — Chu Chuan Liu
(74) *Attorney, Agent, or Firm* — Sughrue Mion, PLLC

(57) ABSTRACT

A probe connected to a pulse photometer include: a first light-emitting portion having a first light-emitting surface from which first light having a first wavelength used for calculating a concentration of a first light-absorbing substance in blood of a patient is emitted; a second light-emitting portion having a second light-emitting surface from which second light having a second wavelength that is used for calculating the concentration of the first light-absorbing substance is emitted; and a third light-emitting portion having a third light-emitting surface from which third light having a third wavelength that is not used for calculating the concentration of the first light-absorbing substance is emitted. A distance between a first reference point of the first light-emitting portion and a second reference point of the second light-emitting portion is shorter than a distance between a third reference point of the third light-emitting portion and the first reference point.

8 Claims, 10 Drawing Sheets

(52) U.S. Cl.
    CPC ............... *A61B 2562/0238* (2013.01); *A61B 2562/0242* (2013.01); *A61B 2562/046* (2013.01)

(58) Field of Classification Search
    CPC ............ A61B 5/0205; A61B 5/02427; A61B 2562/046; A61B 2562/0238; A61B 2562/0242; A61B 2562/0233
    See application file for complete search history.

(56) References Cited

U.S. PATENT DOCUMENTS

| | | | |
|---|---|---|---|
| 6,622,095 B2 | 9/2003 | Kobayashi et al. | |
| 8,320,981 B1* | 11/2012 | Mayer ................ | A61B 5/14551 600/326 |
| 2002/0042558 A1 | 4/2002 | Mendelson | |
| 2003/0144584 A1 | 7/2003 | Mendelson | |
| 2011/0082355 A1 | 4/2011 | Eisen et al. | |
| 2014/0275891 A1* | 9/2014 | Muehlemann ..... | A61B 5/14553 600/328 |
| 2014/0276013 A1 | 9/2014 | Muehlemann et al. | |
| 2014/0276014 A1 | 9/2014 | Khanicheh et al. | |
| 2015/0272488 A1 | 10/2015 | Ueda et al. | |
| 2020/0345238 A1* | 11/2020 | Perälä ................ | A61B 5/14552 |
| 2021/0015365 A1 | 1/2021 | Muehlemann et al. | |

FOREIGN PATENT DOCUMENTS

| | | |
|---|---|---|
| JP | 2005-253478 A | 9/2005 |
| JP | 2015-192865 A | 11/2015 |
| JP | 2016-517307 A | 6/2016 |
| WO | 02/28274 A1 | 4/2002 |
| WO | 2014/165022 A2 | 10/2014 |
| WO | 2020/106060 A1 | 5/2020 |

OTHER PUBLICATIONS

Communication issued on Jan. 23, 2024 by the Japanese Patent Office for Japanese Patent Application No. 2020-151260.

* cited by examiner

PROBE AND PULSE PHOTOMETRY SYSTEM

CROSS-REFERENCE TO RELATED APPLICATIONS

This application claims priority from Japanese Patent Application No. 2020-151260 filed on Sep. 9, 2020, the entire contents of which are incorporated herein by reference.

TECHNICAL FIELD

The presently disclosed subject matter relates to a probe configured to be connected to a pulse photometer that calculates a concentration of a light-absorbing substance in blood of a patient. The presently disclosed subject matter also relates to a pulse photometry system including the probe and the pulse photometer.

BACKGROUND

A probe configured to be connected to a pulse photometer that calculates a concentration of a light-absorbing substance in blood of a patient is disclosed in JP-A-2015-192865. The probe can include at least three light-emitting portions. A wavelength of light emitted from each light-emitting portion is different from a wavelength of light emitted from the other light-emitting portion. According to a principle of the pulse photometry, a concentration of a specific light-absorbing substance in blood can be calculated using two wavelengths. The two wavelengths are determined such that a significant difference appears in an absorbance of the light-absorbing substance. The probe described in JP-A-2015-192865 uses three or more wavelengths in order to improve calculation accuracy of the concentration of the specific light-absorbing substance.

SUMMARY

An object of the presently disclosed subject matter is to prevent a decrease in calculation accuracy of a concentration of a light-absorbing substance in blood by pulse photometry.

A probe according to a first aspect of the presently disclosed subject matter is a probe configured to be connected to a pulse photometer. The probe includes: a first light-emitting portion having a first light-emitting surface from which first light having a first wavelength is emitted, the first wavelength being used for calculating a concentration of a first light-absorbing substance in blood of a patient; a second light-emitting portion having a second light-emitting surface from which second light having a second wavelength that is different from the first wavelength is emitted, the second wavelength being used for calculating the concentration of the first light-absorbing substance; and a third light-emitting portion having a third light-emitting surface from which third light having a third wavelength that is different from the first wavelength and the second wavelength is emitted, the third wavelength being not used for calculating the concentration of the first light-absorbing substance. A distance between a first reference point of the first light-emitting portion when viewed from a normal line direction of the first light-emitting surface and a second reference point of the second light-emitting portion when viewed from a normal line direction of the second light-emitting surface is shorter than a distance between a third reference point of the third light-emitting portion when viewed from a normal line direction of the third light-emitting surface and the first reference point.

A pulse photometry system according to a second aspect of the presently disclosed subject matter includes: a first light-emitting portion having a first light-emitting surface from which first light having a first wavelength is emitted; a second light-emitting portion having a second light-emitting surface from which second light having a second wavelength that is different from the first wavelength is emitted; a third light-emitting portion having a third light-emitting surface from which third light having a third wavelength that is different from the first wavelength and the second wavelength is emitted; a light-detecting portion configured to output a first signal corresponding to an intensity of the first light that has passed through a tissue of a patient, a second signal corresponding to an intensity of the second light that has passed through the tissue, and a third signal corresponding to an intensity of the third light that has passed through the tissue; and a processor configured to calculate a concentration of a first light-absorbing substance in blood of the patient based on the first signal and the second signal and not based on the third signal. A distance between a first reference point of the first light-emitting portion when viewed from a normal line direction of the first light-emitting surface and a second reference point of the second light-emitting portion when viewed from a normal line direction of the second light-emitting surface is shorter than a distance between a third reference point of the third light-emitting portion when viewed from a normal line direction of the third light-emitting surface and the first reference point.

According to the configuration of each of the above aspects, an influence of light emitted from a light-emitting portion not used for calculating the concentration of the first light-absorbing substance on a light-emitting portion used for calculating the concentration of the first light-absorbing substance can be reduced. Therefore, it is possible to prevent a decrease in calculation accuracy of the concentration of the light-absorbing substance by pulse photometry.

DETAILED DESCRIPTION

Examples of an embodiment will be described in detail below with reference to the accompanying drawings. In the accompanying drawings, a scale is appropriately changed in order to make each member have a recognizable size.

Figure 1:
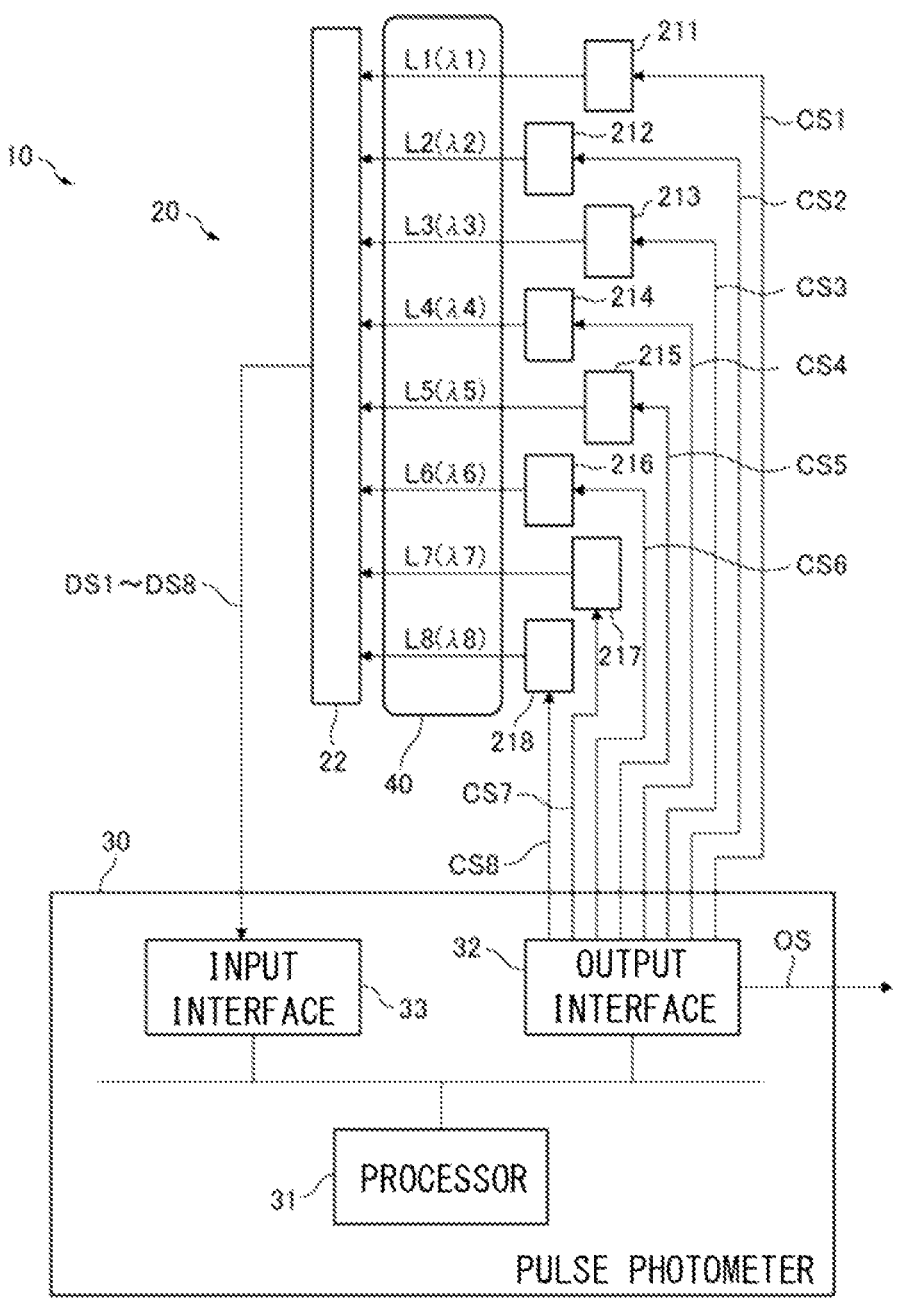
FIG. 1 exemplifies a configuration of a pulse photometry system according to an embodiment.

FIG. 1 exemplifies a configuration of a pulse photometry system 10 according to an embodiment. The pulse photometry system 10 can include a probe 20 and a pulse photometer 30.

The probe 20 can include a first light-emitting portion 211, a second light-emitting portion 212, a third light-emitting portion 213, a fourth light-emitting portion 214, a fifth light-emitting portion 215, a sixth light-emitting portion 216, a seventh light-emitting portion 217, and an eighth light-emitting portion 218. Each of the first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, and the eighth light-emitting portion 218 can include a light emitter. Examples of the light emitter include a light-emitting diode (LED), a laser diode (LD), and an EL element.

The first light-emitting portion 211 is configured to emit first light L1 having a first wavelength $\lambda 1$. The first light-emitting portion 211 may include a light emitter that emits light having the first wavelength $\lambda 1$, or may be configured to emit light having the first wavelength $\lambda 1$ by causing light having a wavelength different from the first wavelength $\lambda 1$ emitted from the light emitter to pass through an appropriate optical element.

The second light-emitting portion 212 is configured to emit second light L2 having a second wavelength $\lambda 2$. The second light-emitting portion 212 may include a light emitter that emits light having the second wavelength $\lambda 2$, or may be configured to emit light having the second wavelength $\lambda 2$ by causing light having a wavelength different from the second wavelength $\lambda 2$ emitted from a light emitter to pass through an appropriate optical element.

The third light-emitting portion 213 is configured to emit third light L3 having a third wavelength $\lambda 3$. The third light-emitting portion 213 may include a light emitter that emits light having the third wavelength $\lambda 3$, or may be configured to emit light having the third wavelength $\lambda 3$ by causing light having a wavelength different from the third wavelength $\lambda 3$ emitted from a light emitter to pass through an appropriate optical element.

The fourth light-emitting portion 214 is configured to emit fourth light L4 having a fourth wavelength $\lambda 4$. The fourth light-emitting portion 214 may include a light emitter that emits light having the fourth wavelength $\lambda 4$, or may be configured to emit light having the fourth wavelength $\lambda 4$ by causing light having a wavelength different from the fourth wavelength $\lambda 4$ emitted from a light emitter to pass through an appropriate optical element.

The fifth light-emitting portion 215 is configured to emit fifth light L5 having a fifth wavelength $\lambda 5$. The fifth light-emitting portion 215 may include a light emitter that emits light having the fifth wavelength $\lambda 5$, or may be configured to emit light having the fifth wavelength $\lambda 5$ by causing light having a wavelength different from the fifth wavelength $\lambda 5$ emitted from a light emitter to pass through an appropriate optical element.

The sixth light-emitting portion 216 is configured to emit sixth light L6 having a sixth wavelength $\lambda 6$. The sixth light-emitting portion 216 include a light emitter that emits light having the sixth wavelength $\lambda 6$, or may be configured to emit light having the sixth wavelength $\lambda 6$ by causing light having a wavelength different from the sixth wavelength $\lambda 6$ emitted from a light emitter to pass through an appropriate optical element.

The seventh light-emitting portion 217 is configured to emit seventh light L7 having a seventh wavelength $\lambda 7$. The seventh light-emitting portion 217 include a light emitter that emits light having the seventh wavelength $\lambda 7$, or may be configured to emit light having the seventh wavelength $\lambda 7$ by causing light having a wavelength different from the seventh wavelength $\lambda 7$ emitted from a light emitter to pass through an appropriate optical element.

The eighth light-emitting portion 218 is configured to emit eighth light L8 having an eighth wavelength $\lambda 8$. The eighth light-emitting portion 218 may include a light emitter that emits light having the eighth wavelength $\lambda 8$, or may be configured to emit light having the eighth wavelength $\lambda 8$ by causing light having a wavelength different from the eighth wavelength $\lambda 8$ emitted from a light emitter to pass through an appropriate optical element.

The first wavelength $\lambda 1$, the second wavelength $\lambda 2$, the third wavelength $\lambda 3$, the fourth wavelength $\lambda 4$, the fifth wavelength $\lambda 5$, the sixth wavelength $\lambda 6$, the seventh wavelength $\lambda 7$, and the eighth wavelength $\lambda 8$ are different from one another.

The probe 20 can include a light-detecting portion 22. The light-detecting portion 22 can include a light detector that outputs a detection signal corresponding to an intensity of incident light. The detection signal may be an analog signal or a digital signal. Examples of the light detector include a photodiode, a phototransistor, and a photoresistor that are sensitive to at least the first wavelength $\lambda 1$, the second wavelength $\lambda 2$, the third wavelength $\lambda 3$, the fourth wavelength $\lambda 4$, the fifth wavelength $\lambda 5$, the sixth wavelength $\lambda 6$, the seventh wavelength $\lambda 7$, and the eighth wavelength $\lambda 8$.

The probe 20 is attachable to a body 40 of a patient. In this example, the first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, the eighth light-emitting portion 218, and the light-detecting portion 22 are arranged such that the first light L1, the second light L2, the third light L3, the fourth light L4, the fifth light L5, the sixth light L6, the seventh light L7, and the eighth light L8 pass through the body 40 and are incident on the light-detecting portion 22.

The first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, the eighth light-emitting portion 218, and the light-detecting portion 22 may be arranged such that the first light L1, the second light L2, the third light L3, the fourth light L4, the fifth light L5, the sixth light L6, the seventh light L7, and the eighth light L8 are reflected by the body 40 and incident on the light-detecting portion 22.

The pulse photometer 30 can include a processor 31, an output interface 32, and an input interface 33.

The processor 31 is configured to control turn-on and turn-off operations of each of the first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, and the eighth light-emitting portion 218.

Specifically, the processor 31 allows a first control signal CS1, a second control signal CS2, a third control signal CS3, a fourth control signal CS4, a fifth control signal CS5, a sixth control signal CS6, a seventh control signal CS7, and an eighth control signal CS8 to be output from the output interface 32.

The first control signal CS1 causes the first light-emitting portion 211 to emit the first light L1. The second control signal CS2 causes the second light-emitting portion 212 to emit the second light L2. The third control signal CS3 causes the third light-emitting portion 213 to emit the third light L3. The fourth control signal CS4 causes the fourth light-emitting portion 214 to emit the fourth light L4. The fifth control signal CS5 causes the fifth light-emitting portion 215 to emit the fifth light L5. The sixth control signal CS6 causes the sixth light-emitting portion 216 to emit the sixth light L6. The seventh control signal CS7 causes the seventh light-emitting portion 217 to emit the seventh light L7. The eighth control signal CS8 causes the eighth light-emitting portion 218 to emit the eighth light L8.

Each of the first control signal CS1, the second control signal CS2, the third control signal CS3, the fourth control signal CS4, the fifth control signal CS5, the sixth control signal CS6, the seventh control signal CS7, and the eighth control signal CS8 may be an analog signal or a digital signal. When each of the first control signal CS1, the second control signal CS2, the third control signal CS3, the fourth control signal CS4, the fifth control signal CS5, the sixth control signal CS6, the seventh control signal CS7, and the eighth control signal CS8 is the analog signal, the output interface 32 may include an appropriate conversion circuit including a D/A converter.

When the first light L1 that has passed through the body 40 is incident on the light-detecting portion 22, the light-detecting portion 22 outputs a first detection signal DS1. When the second light L2 that has passed through the body 40 is incident on the light-detecting portion 22, the light-detecting portion 22 outputs a second detection signal DS2. When the third light L3 that has passed through the body 40 is incident on the light-detecting portion 22, the light-detecting portion 22 outputs a third detection signal DS3. When the fourth light L4 that has passed through the body 40 is incident on the light-detecting portion 22, the light-detecting portion 22 outputs a fourth detection signal DS4. When the fifth light L5 that has passed through the body 40 is incident on the light-detecting portion 22, the light-detecting portion 22 outputs a fifth detection signal DS5. When the sixth light L6 that has passed through the body 40 is incident on the light-detecting portion 22, the light-detecting portion 22 outputs a sixth detection signal DS6. When the seventh light L7 that has passed through the body 40 is incident on the light-detecting portion 22, the light-detecting portion 22 outputs a seventh detection signal DS7. When the eighth light L8 that has passed through the body 40 is incident on the light-detecting portion 22, the light-detecting portion 22 outputs an eighth detection signal DS8.

The input interface 33 is configured to receive each of the first detection signal DS1, the second detection signal DS2, the third detection signal DS3, the fourth detection signal DS4, the fifth detection signal DS5, the sixth detection signal DS6, the seventh detection signal DS7, and the eighth detection signal DS8 output from the light-detecting portion 22. When each of the first detection signal DS1, the second detection signal DS2, the third detection signal DS3, the fourth detection signal DS4, the fifth detection signal DS5, the sixth detection signal DS6, the seventh detection signal DS7, and the eighth detection signal DS8 is the analog signal, the input interface 33 can include an appropriate conversion circuit including an A/D converter.

Figure 2:
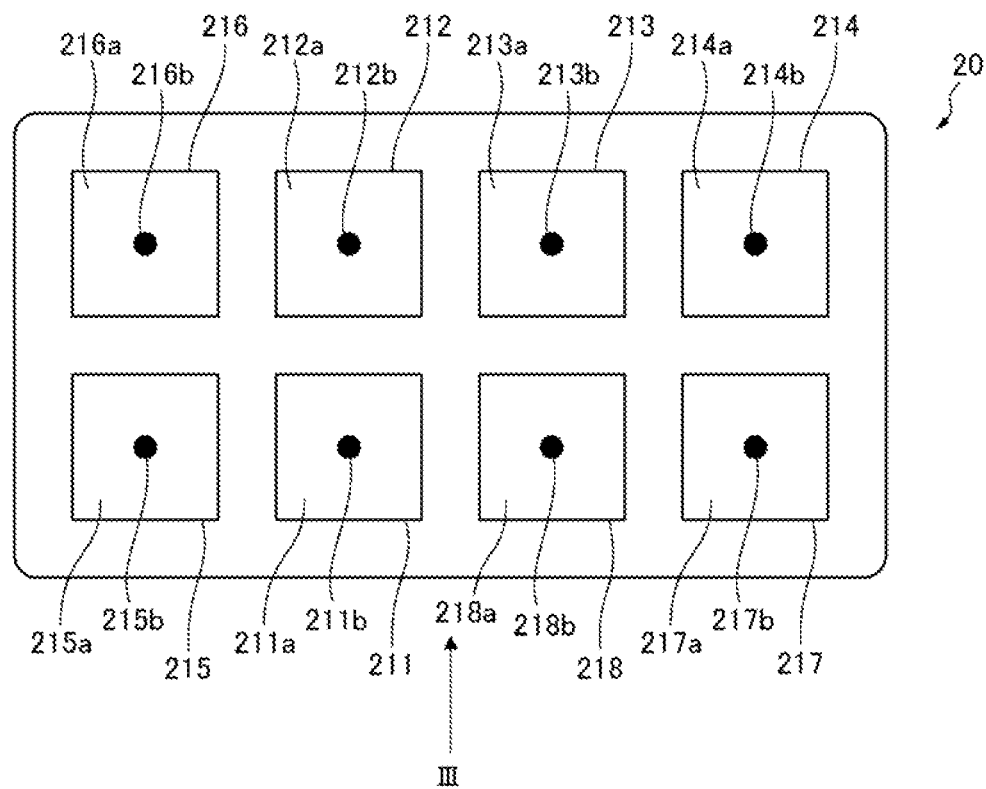
FIG. 2 illustrates an example of a configuration of light-emitting portions in a probe of FIG. 1.

FIG. 2 illustrates an example of an arrangement of the first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, and the eighth light-emitting portion 218 in the probe 20.

The first light-emitting portion 211 can have a first light-emitting surface 211a. The first light-emitting surface 211a is a surface from which light emitted from a light emitter provided in the first light-emitting portion 211 is emitted, and forms a part of an outer surface of the probe 20.

The second light-emitting portion 212 can have a second light-emitting surface 212a. The second light-emitting surface 212a is a surface from which light emitted from a light emitter provided in the second light-emitting portion 212 is emitted, and forms a part of the outer surface of the probe 20.

The third light-emitting portion 213 can have a third light-emitting surface 213a. The third light-emitting surface 213a is a surface from which light emitted from a light emitter provided in the third light-emitting portion 213 is emitted, and forms a part of the outer surface of the probe 20.

The fourth light-emitting portion 214 can have a fourth light-emitting surface 214a. The fourth light-emitting surface 214a is a surface from which light emitted from a light emitter provided in the fourth light-emitting portion 214 is emitted, and forms a part of the outer surface of the probe 20.

The fifth light-emitting portion 215 can have a fifth light-emitting surface 215a. The fifth light-emitting surface 215a is a surface from which light emitted from a light emitter provided in the fifth light-emitting portion 215 is emitted, and forms a part of the outer surface of the probe 20.

The sixth light-emitting portion 216 can have a sixth light-emitting surface 216a. The sixth light-emitting surface 216a is a surface from which light emitted from a light emitter provided in the sixth light-emitting portion 216 is emitted, and forms a part of the outer surface of the probe 20.

The seventh light-emitting portion 217 can have a seventh light-emitting surface 217a. The seventh light-emitting surface 217a is a surface from which light emitted from a light emitter provided in the seventh light-emitting portion 217 is emitted, and forms a part of the outer surface of the probe 20.

The eighth light-emitting portion 218 can have an eighth light-emitting surface 218a. The eighth light-emitting surface 218a is a surface from which light emitted from a light emitter provided in the eighth light-emitting portion 218 is emitted, and forms a part of the outer surface of the probe 20.

Figure 3:
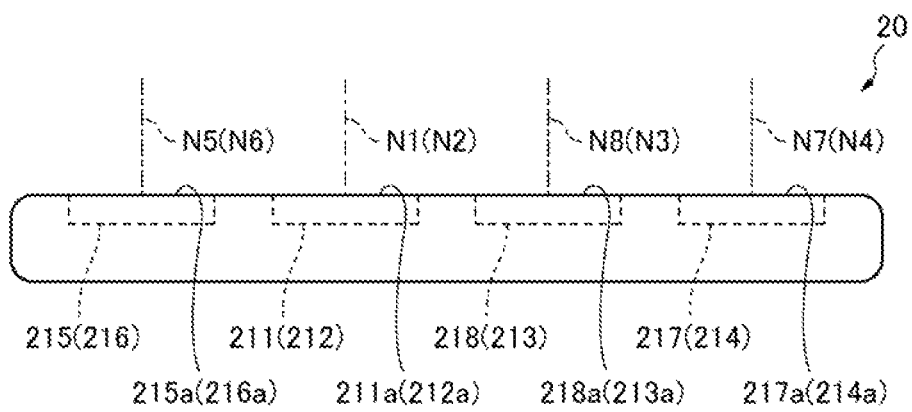
FIG. 3 illustrates an example of the configuration of the light-emitting portions in the probe of FIG. 1.

FIG. 3 exemplifies an appearance of a part of the probe 20 when viewed from a direction of an arrow III in FIG. 2. A first normal line N1, a fifth normal line N5, a seventh normal line N7, and an eighth normal line N8 can be defined for the first light-emitting surface 211a, the fifth light-emitting surface 215a, the seventh light-emitting surface 217a, and the eighth light-emitting surface 218a, respectively. Although not illustrated, a second normal line N2, a third normal line N3, a fourth normal line N4, and a sixth normal line N6 can also be defined for the second light-emitting surface 212a, the third light-emitting surface 213a, the fourth light-emitting surface 214a, and the sixth light-emitting surface 216a, respectively.

That is, FIG. 2 exemplifies an appearance of the first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, and the eighth light-emitting portion 218 when viewed from directions along the first normal line N1, the second normal line N2, the third normal line N3, the fourth normal line N4, the fifth normal line N5, the sixth normal line N6, the seventh normal line N7, and the eighth normal line N8. When viewed from the same direction, the first light-emitting surface 211a, the second light-emitting surface 212a, the third light-emitting surface 213a, the fourth light-emitting surface 214a, the fifth light-emitting surface 215a, the sixth light-emitting surface 216a, the seventh light-emitting surface 217a, and the eighth light-emitting surface 218a have the same shape.

The first light-emitting portion 211 can have a first reference point 211b. The first reference point 211b is defined as a central portion of the first light-emitting surface 211a when viewed from a direction in which the first normal line N1 extends.

The second light-emitting portion 212 can have a second reference point 212b. The second reference point 212b is defined as a central portion of the second light-emitting surface 212a when viewed from a direction in which the second normal line N2 extends.

The third light-emitting portion 213 can have a third reference point 213b. The third reference point 213b is defined as a central portion of the third light-emitting surface 213a when viewed from a direction in which the third normal line N3 extends.

The fourth light-emitting portion 214 can have a fourth reference point 214b. The fourth reference point 214b is defined as a central portion of the fourth light-emitting surface 214a when viewed from a direction in which the fourth normal line N4 extends.

The fifth light-emitting portion 215 can have a fifth reference point 215b. The fifth reference point 215b is defined as a central portion of the fifth light-emitting surface 215a when viewed from a direction in which the fifth normal line N5 extends.

The sixth light-emitting portion 216 can have a sixth reference point 216b. The sixth reference point 216b is defined as a central portion of the sixth light-emitting surface 216a when viewed from a direction in which the sixth normal line N6 extends.

The seventh light-emitting portion 217 can have a seventh reference point 217b. The seventh reference point 217b is defined as a central portion of the seventh light-emitting surface 217a when viewed from a direction in which the seventh normal line N7 extends.

The eighth light-emitting portion 218 can have an eighth reference point 218b. The eighth reference point 218b is defined as a central portion of the eighth light-emitting surface 218a when viewed from a direction in which the eighth normal line N8 extends.

However, the first reference point 211b, the second reference point 212b, the third reference point 213b, the fourth reference point 214b, the fifth reference point 215b, the sixth reference point 216b, the seventh reference point 217b, and the eighth reference point 218b may be defined at appropriate positions as long as the same conditions are satisfied for each light-emitting surface. For example, an upper right corner of each light-emitting surface may be defined as the reference point.

Figure 4:
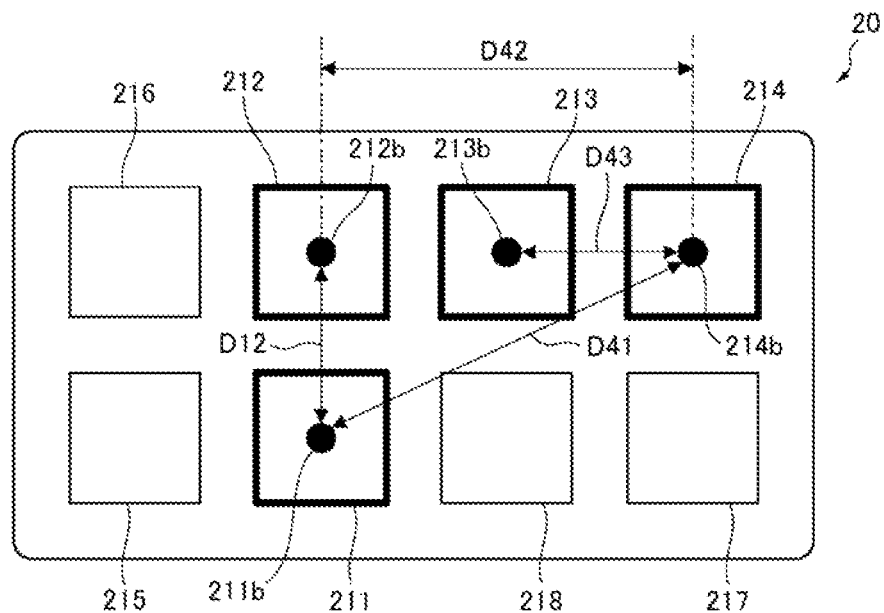
FIG. 4 illustrates an example of an operation of the light-emitting portions of FIG. 2.

An example of an operation of the pulse photometry system 10 configured as described above will be described with reference to FIG. 4. In this example, the pulse photometer 30 calculates a concentration Φo of oxyhemoglobin (O2Hb) and a concentration Φc of carboxyhemoglobin (COHb). The oxyhemoglobin is an example of a first light-absorbing substance in blood. The carboxyhemoglobin is an example of a second light-absorbing substance in blood.

In this example, in order to calculate the concentration Φo of the oxyhemoglobin, the first light-emitting portion 211 and the second light-emitting portion 212 are used. The oxyhemoglobin has wavelength dependence on an absorbance. The first wavelength λ1 and the second wavelength λ2 are determined as two wavelengths at which a significant difference appears in the absorbance of the oxyhemoglobin. The first wavelength λ1 is an example of the first wavelength used for calculating a concentration of a first light absorber. The second wavelength λ2 is an example of the second wavelength used for calculating the concentration of the first light absorber.

The first light L1 emitted from the first light-emitting portion 211 is absorbed by arterial blood, venous blood, tissue, or the like when passing through the body 40 of the patient. Therefore, an intensity of the first light L1 incident on the light-detecting portion 22 is lower than an intensity during emission from the first light-emitting portion 211. That is, an absorbance A1 of the first light L1 can be defined as a ratio between an intensity of light emitted from the first light-emitting portion 211 and an intensity of light incident on the light-detecting portion 22.

Same or similarly, the second light L2 emitted from the second light-emitting portion 212 is absorbed by the arterial blood, the venous blood, the tissue, or the like when passing through the body 40 of the patient. Therefore, an intensity of the second light L2 incident on the light-detecting portion 22 is lower than an intensity during emission from the first light-emitting portion 211. That is, an absorbance A2 of the second light L2 can be defined as a ratio between an intensity of light emitted from the second light-emitting portion 212 and an intensity of light incident on the light-detecting portion 22.

An arterial blood vessel pulsates with pulsation of a heart of the patient to change thickness of the arterial blood vessel through which the first light L1 and the second light L2 pass changes. In other words, an amount of the arterial blood that absorbs the first light L1 and the second light L2 changes. Therefore, with pulsation of blood of the patient, the intensity of the first light L1 incident on the light-detecting portion 22 and the intensity of the second light L2 incident on the light-detecting portion 22 change, and the absorbance A1 of the first light L1 and the absorbance A2 of the second light L2 change. A change amount of each absorbance is defined as a first change amount $\Delta A1$ and a second change amount $\Delta A2$.

The concentration $\Phi o$ of the oxyhemoglobin is calculated based on a ratio ($\Delta A1/\Delta A2$) between the first change amount $\Delta A1$ and the second change amount $\Delta A2$. That is, the processor 31 of the pulse photometer 30 calculates the concentration $\Phi o$ of the oxyhemoglobin based on the first detection signal DS1 and the second detection signal DS2 output from the light-detecting portion 22.

The processor 31 can output a signal OS corresponding to the concentration $\Phi o$ of the oxyhemoglobin from the output interface 32. The signal is subjected to an appropriate processing. Examples of such a processing include calculation of a value that can be acquired based on the concentration $\Phi o$, display of at least one of a value of the concentration $\Phi o$ and the value acquired based on the concentration $\Phi o$, and a notification operation based on at least one of the value of the concentration $\Phi o$ and the value acquired based on the concentration $\Phi o$. Examples of the value that can be acquired based on the concentration $\Phi o$ include percutaneous arterial oxygen saturation (SpO2).

In this example, in order to calculate the concentration $\Phi c$ of the carboxyhemoglobin, the third light-emitting portion 213 and the fourth light-emitting portion 214 are used. The carboxyhemoglobin has wavelength dependence on an absorbance. The third wavelength $\lambda 3$ and the fourth wavelength $\lambda 4$ are determined as two wavelengths at which a significant difference appears in the absorbance of the carboxyhemoglobin. The fourth wavelength $\lambda 4$ is an example of the third wavelength not used for calculating the concentration of the first light-absorbing substance. The fourth wavelength $\lambda 4$ is also an example of the third wavelength used for calculating the concentration of the second light-absorbing substance. The third wavelength $\lambda 3$ is an example of the fourth wavelength not used for calculating the concentration of the first light-absorbing substance. The third wavelength $\lambda 3$ is also an example of the fourth wavelength used for calculating the concentration of the second light-absorbing substance.

Also, for the third light L3 and the fourth light L4, an absorbance A3 and an absorbance A4 accompanying the passage through the body 40 of the patient can be obtained, and a third change amount $\Delta A3$ and a fourth change amount $\Delta A4$ accompanying the pulsation can be defined. The concentration $\Phi c$ of the carboxyhemoglobin is calculated based on a ratio ($\Delta A3/\Delta A4$) between the third change amount $\Delta A3$ and the fourth change amount $\Delta A4$. That is, the processor 31 of the pulse photometer 30 calculates the concentration $\Phi c$ of the carboxyhemoglobin based on the third detection signal DS3 and the fourth detection signal DS4 output from the light-detecting portion 22.

The processor 31 can output a signal OS corresponding to the concentration $\Phi c$ of the carboxyhemoglobin from the output interface 32. The signal OS is subjected to an appropriate processing. Examples of such a processing include calculation of a value that can be acquired based on the concentration $\Phi c$, display of at least one of a value of the concentration $\Phi c$ and the value acquired based on the concentration $\Phi c$, and a notification operation based on at least one of the value of the concentration $\Phi c$ and the value acquired based on the concentration $\Phi c$.

In this example, the first light-emitting portion 211, the second light-emitting portion 212, the third light-emitting portion 213, and the fourth light-emitting portion 214 are arranged so as to satisfy the following conditions.

A distance D12 between the first reference point 211b and the second reference point 212b is shorter than a distance D41 between the fourth reference point 214b and the first reference point 211b.

The distance D12 between the first reference point 211b and the second reference point 212b is shorter than a distance D42 between the fourth reference point 214b and the second reference point 212b.

A distance D43 between the fourth reference point 214b and the third reference point 213b is shorter than the distance D41 between the fourth reference point 214b and the first reference point 211b.

The distance D43 between the fourth reference point 214b and the third reference point 213b is shorter than the distance D42 between the fourth reference point 214b and the second reference point 212b.

According to the above-described configuration, the first light-emitting portion 211 and the second light-emitting portion 212 used to calculate the concentration $\Phi o$ of the oxyhemoglobin can be arranged closer to each other, and the third light-emitting portion 213 and the fourth light-emitting portion 214 used to calculate the concentration $\Phi c$ of the carboxyhemoglobin can be arranged closer to each other.

Accordingly, for each of the concentration $\Phi o$ of the oxyhemoglobin and the concentration $\Phi c$ of the carboxyhemoglobin, an influence of a difference in an optical path length from a plurality of light-emitting portions to the light-detecting portion 22 used for calculation on a change in an absorbance due to the pulsation can be reduced. Therefore, it is possible to prevent a decrease in calculation accuracy of the concentration of the light-absorbing substance by pulse photometry.

Figure 5:
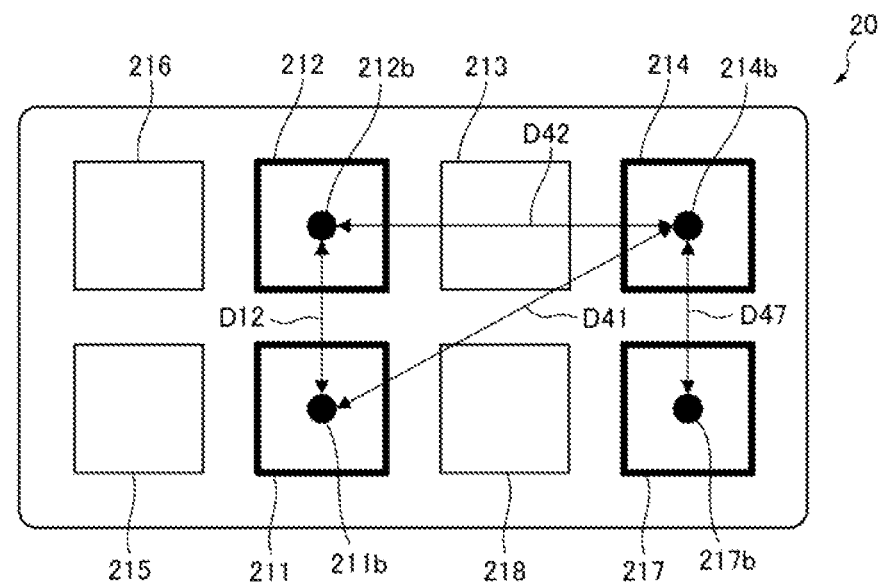
FIG. 5 illustrates another example of the operation of the light-emitting portions of FIG. 2.

As exemplified in FIG. 5, the seventh light-emitting portion 217 can be used to calculate the concentration $\Phi c$ of the carboxyhemoglobin. The seventh wavelength $\lambda 7$ is determined as a wavelength at which a significant difference appears in the absorbance of the carboxyhemoglobin with respect to at least one of the third wavelength $\lambda 3$ and the fourth wavelength $\lambda 4$. The seventh wavelength $\lambda 7$ is an example of the fourth wavelength not used for calculating the concentration of the first light-absorbing substance. The seventh wavelength $\lambda 7$ is also an example of the fourth wavelength used for calculating the concentration of the second light-absorbing substance. Also, for the seventh light L7, an absorbance A7 accompanying the passage through the body 40 of the patient can be obtained, and a seventh change amount $\Delta A7$ accompanying the pulsation can be defined.

The seventh light-emitting portion 217 may be used in addition to the third light-emitting portion 213 and the fourth light-emitting portion 214, or may be used in place of one of the third light-emitting portion 213 and the fourth light-emitting portion 214. In the former case, by using the seventh change amount $\Delta A7$ as an offset term for a calculation result of the ratio between the third change amount $\Delta A3$ and the fourth change amount $\Delta A4$, it is possible to prevent an influence of other light-absorbing substances and to improve calculation accuracy of the concentration $\Phi c$ of the carboxyhemoglobin. In the latter case, when the concentration $\Phi c$ of the carboxyhemoglobin cannot be appropriately calculated by the third light-emitting portion 213 and the fourth light-emitting portion 214 due to various reasons, it is possible to attempt to calculate the concentration $\Phi c$ of the carboxyhemoglobin by using the seventh light-emitting portion 217 as an alternative light source.

In this example, the first light-emitting portion 211, the second light-emitting portion 212, the fourth light-emitting portion 214, and the seventh light-emitting portion 217 are arranged so as to satisfy the following conditions.

The distance D12 between the first reference point 211b and the second reference point 212b is shorter than the distance D41 between the fourth reference point 214b and the first reference point 211b.

The distance D12 between the first reference point 211b and the second reference point 212b is shorter than the distance D42 between the fourth reference point 214b and the second reference point 212b.

A distance D47 between the fourth reference point 214b and the seventh reference point 217b is shorter than the distance D41 between the fourth reference point 214b and the first reference point 211b.

The distance D47 between the fourth reference point 214b and the seventh reference point 217b is shorter than the distance D42 between the fourth reference point 214b and the second reference point 212b.

According to the above-described configuration, the first light-emitting portion 211 and the second light-emitting portion 212 used to calculate the concentration $\Phi$o of the oxyhemoglobin can be arranged closer to each other, and the fourth light-emitting portion 214 and the seventh light-emitting portion 217 used to calculate the concentration $\Phi$c of the carboxyhemoglobin can be arranged closer to each other.

Accordingly, for each of the concentration $\Phi$o of the oxyhemoglobin and the concentration $\Phi$c of the carboxyhemoglobin, an influence of a difference in an optical path length from a plurality of light-emitting portions to the light-detecting portion 22 used for calculation on a change in an absorbance due to the pulsation can be reduced. Therefore, it is possible to prevent a decrease in calculation accuracy of the concentration of the blood light absorber by pulse photometry.

Figure 6:
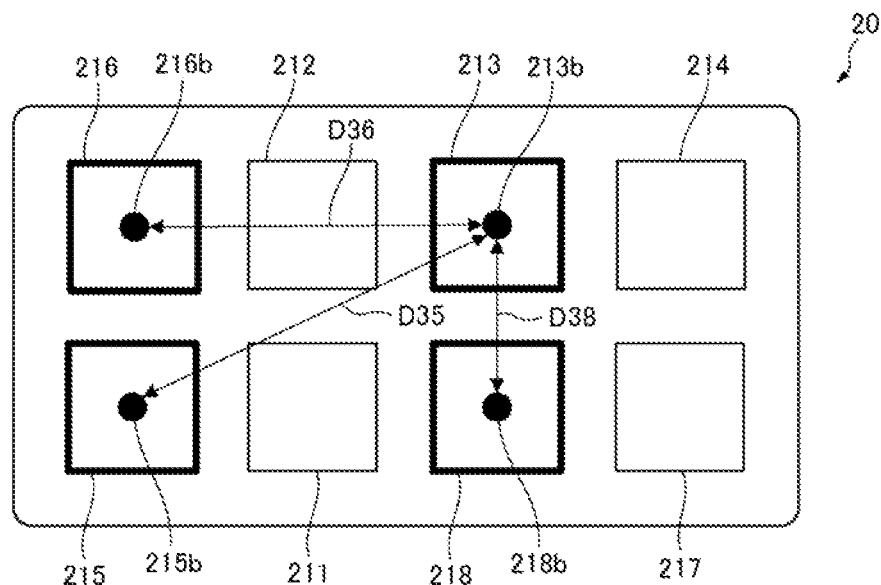
FIG. 6 illustrates another example of the operation of the light-emitting portions of FIG. 2.

FIG. 6 illustrates another example of the operation of the pulse photometry system 10. In this example, the pulse photometer 30 calculates a concentration $\Phi$r of deoxyhemoglobin (RHb). The deoxyhemoglobin is an example of the first light-absorbing substance in blood.

In this example, in order to calculate the concentration $\Phi$r of the deoxyhemoglobin, the third light-emitting portion 213 and the eighth light-emitting portion 218 are used. The deoxyhemoglobin has wavelength dependence on an absorbance. The eighth wavelength $\lambda 8$ is determined as a wavelength at which a significant difference appears in an absorbance of the deoxyhemoglobin with respect to the third wavelength $\lambda 3$. The third wavelength $\lambda 3$ is an example of the first wavelength used for calculating the concentration of the first light absorber. The eighth wavelength $\lambda 8$ is an example of the second wavelength used for calculating the concentration of the first light absorber.

Also, for the eighth light L8, an absorbance A8 accompanying the passage through the body 40 of the patient can be obtained, and an eighth change amount $\Delta A8$ accompanying the pulsation can be defined. The concentration $\Phi$r of the deoxyhemoglobin is calculated based on a ratio ($\Delta A3/\Delta A8$) between the third change amount $\Delta A3$ and the eighth change amount $\Delta A8$. That is, the processor 31 of the pulse photometer 30 calculates the concentration $\Phi$r of the deoxyhemoglobin based on the third detection signal DS3 and the eighth detection signal DS8 output from the light-detecting portion 22.

The processor 31 can output a signal OS corresponding to the concentration $\Phi$r of the deoxyhemoglobin from the output interface 32. The signal OS is subjected to an appropriate processing. Examples of such a processing include calculation of a value that can be acquired based on the concentration $\Phi$r, display of at least one of a value of the concentration $\Phi$r and the value acquired based on the concentration $\Phi$r, and a notification operation based on at least one of the value of the concentration $\Phi$r and the value acquired based on the concentration $\Phi$r. When it is assumed that there is no abnormal hemoglobin such as carboxyhemoglobin or methemoglobin in hemoglobin in the arterial blood, the concentration of the oxyhemoglobin can be specified by specifying the concentration of the deoxyhemoglobin. In this case, examples of the value that can be acquired based on the concentration $\Phi$r include the percutaneous arterial oxygen saturation (SpO2).

In a case where it can be assumed that two types of light absorbers exist in a blood system, another example of the relationship in which one concentration can be specified and the other concentration can be specified is a relationship between a concentration of total hemoglobin and a concentration of water in blood.

In this example, at least one of the fifth light-emitting portion 215 and the sixth light-emitting portion 216 is used to determine an attachment state of the probe 20 to the body 40 of the patient. For example, when at least one of an intensity of the fifth light L5 incident on the light-detecting portion 22 and an intensity of the sixth light L6 incident on the light-detecting portion 22 is smaller than a threshold, the processor 31 of the pulse photometer 30 determines that the attachment state of the probe 20 to the body 40 of the patient is not appropriate. Each of the fifth wavelength $\lambda 5$ and the sixth wavelength $\lambda 6$ is an example of the third wavelength not used for calculating the concentration of the first light-absorbing substance.

In this example, the fifth light-emitting portion 215, the sixth light-emitting portion 216, the third light-emitting portion 213, and the eighth light-emitting portion 218 are arranged so as to satisfy the following conditions.

A distance D38 between the third reference point 213b and the eighth reference point 218b is shorter than a distance D35 between the third reference point 213b and the fifth reference point 215b.

The distance D38 between the third reference point 213b and the eighth reference point 218b is shorter than a distance D36 between the third reference point 213b and the sixth reference point 216b.

According to the above-described configuration, an influence of light emitted from a light-emitting portion not used for calculating the concentration $\Phi$r of the deoxyhemoglobin on a light-emitting portion used for calculating the concentration $\Phi$r of the deoxyhemoglobin can be reduced. Therefore, it is possible to prevent a decrease in calculation accuracy of the concentration of the light-absorbing substance by pulse photometry.

Figure 7:
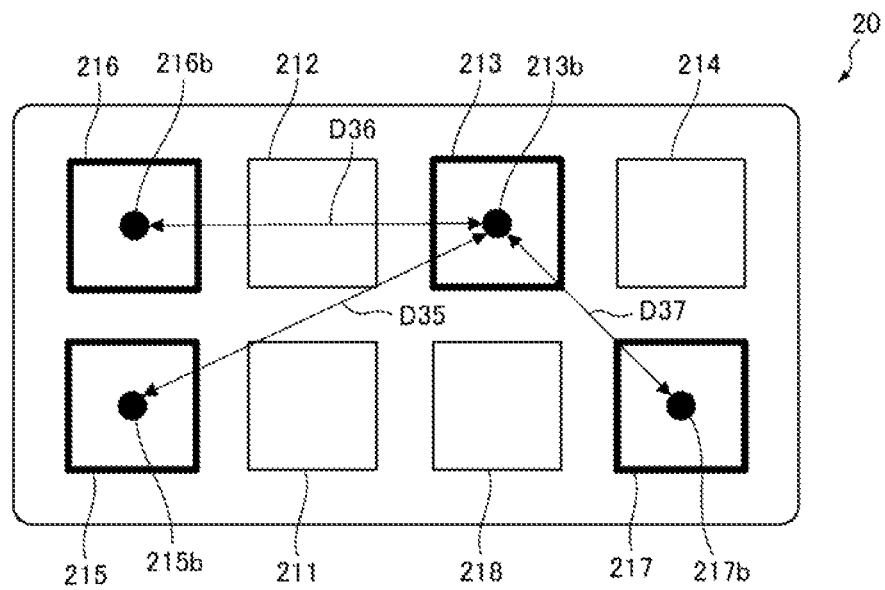
FIG. 7 illustrates another example of the operation of the light-emitting portions of FIG. 2.

As exemplified in FIG. 7, the seventh light-emitting portion 217 can be used to calculate the concentration $\Phi$r of the deoxyhemoglobin. The seventh wavelength $\lambda 7$ is determined as a wavelength at which a significant difference appears in the absorbance of the deoxyhemoglobin with respect to at least one of the third wavelength $\lambda 3$ and the eighth wavelength $\lambda 8$. The seventh wavelength $\lambda 7$ is an example of the second wavelength used for calculating the concentration of the first light absorber.

The seventh light-emitting portion 217 may be used in addition to the third light-emitting portion 213 and the eighth light-emitting portion 218, or may be used in place of one of the third light-emitting portion 213 and the eighth light-emitting portion 218. In the former case, by using the seventh change amount $\Delta A7$ as an offset term for a calculation result of the ratio between the third change amount ΔA3 and the eighth change amount ΔA8, it is possible to prevent an influence of other light-absorbing substances and to improve calculation accuracy of the concentration Φr of the deoxyhemoglobin. In the latter case, when the concentration Φr of the deoxyhemoglobin cannot be appropriately calculated by the third light-emitting portion 213 and the eighth light-emitting portion 218 due to various reasons, it is possible to attempt to calculate the concentration Φr of the deoxyhemoglobin by using the seventh light-emitting portion 217 as an alternative light source.

In this example, the fifth light-emitting portion 215, the sixth light-emitting portion 216, the third light-emitting portion 213, and the seventh light-emitting portion 217 are arranged so as to satisfy the following conditions.

A distance D37 between the third reference point 213b and the seventh reference point 217b is shorter than the distance D35 between the third reference point 213b and the fifth reference point 215b.

The distance D37 between the third reference point 213b and the seventh reference point 217b is shorter than the distance D36 between the third reference point 213b and the sixth reference point 216b.

According to the above-described configuration as well, an influence of light emitted from a light-emitting portion not used for calculating the concentration Φr of the deoxyhemoglobin on a light-emitting portion used for calculating the concentration Φr of the deoxyhemoglobin can also be reduced. Therefore, it is possible to prevent a decrease in calculation accuracy of the concentration of the light-absorbing substance by pulse photometry.

Figure 8:
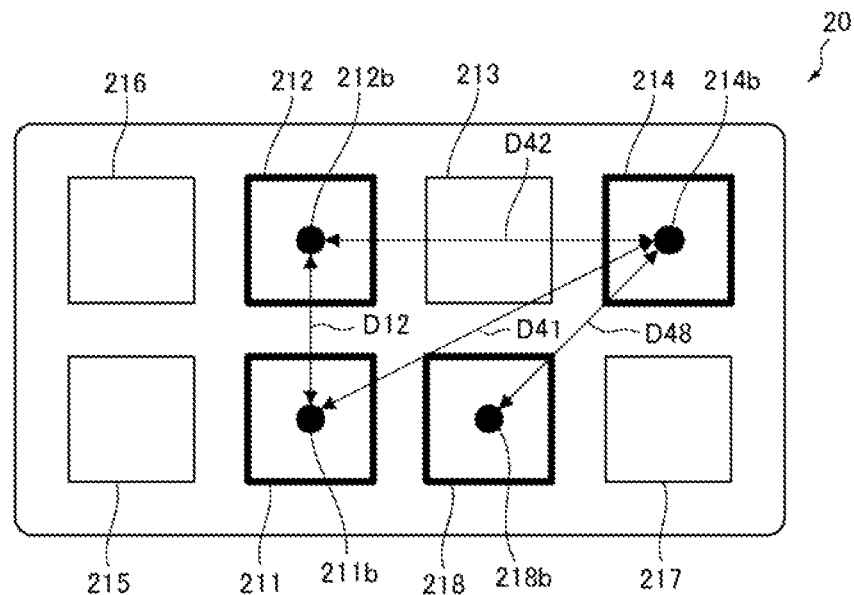
FIG. 8 illustrates another example of the operation of the light-emitting portions of FIG. 2.

FIG. 8 illustrates another example of the operation of the pulse photometry system 10. In this example, the pulse photometer 30 calculates the concentration Φo of the oxyhemoglobin (O2Hb) and a concentration Φm of the methemoglobin (MetHb). The oxyhemoglobin is an example of the first light-absorbing substance in blood. The methemoglobin is an example of the second light-absorbing substance in blood.

In this example, in order to calculate the concentration Φo of the oxyhemoglobin, the first light-emitting portion 211 and the second light-emitting portion 212 are used. Since the calculation method is the same as the example described with reference to FIGS. 4 and 5, the repeated description will be omitted.

In this example, in order to calculate the concentration Φm of the methemoglobin, the fourth light-emitting portion 214 and the eighth light-emitting portion 218 are used. The methemoglobin has wavelength dependence on an absorbance. The fourth wavelength λ4 and the eighth wavelength λ8 are determined as two wavelengths at which a significant difference appears in the absorbance of the methemoglobin. The fourth wavelength λ4 is an example of the third wavelength not used for calculating the concentration of the first light-absorbing substance. The fourth wavelength λ4 is also an example of the third wavelength used for calculating the concentration of the second light-absorbing substance. The eighth wavelength λ8 is an example of the fourth wavelength not used for calculating the concentration of the first light-absorbing substance. The eighth wavelength λ8 is also an example of the fourth wavelength used for calculating the concentration of the second light-absorbing substance.

The concentration Φm of the methemoglobin is calculated based on a ratio (ΔA4/ΔA8) between the fourth change amount ΔA4 and the eighth change amount ΔA8. That is, the processor 31 of the pulse photometer 30 calculates the concentration Φm of the methemoglobin based on the fourth detection signal DS4 and the eighth detection signal DS8 output from the light-detecting portion 22.

The processor 31 can output a signal OS corresponding to the concentration Φm of the methemoglobin from the output interface 32. The signal OS is subjected to an appropriate processing. Examples of such a processing include calculation of a value that can be acquired based on the concentration Φm, display of at least one of a value of the concentration Φm and the value acquired based on the concentration Φm, and a notification operation based on at least one of the value of the concentration Φm and the value acquired based on the concentration Φm.

In this example, the first light-emitting portion 211, the second light-emitting portion 212, the fourth light-emitting portion 214, and the eighth light-emitting portion 218 are arranged so as to satisfy the following conditions.

The distance D12 between the first reference point 211b and the second reference point 212b is shorter than the distance D41 between the fourth reference point 214b and the first reference point 211b.

The distance D12 between the first reference point 211b and the second reference point 212b is shorter than the distance D42 between the fourth reference point 214b and the second reference point 212b.

The distance D48 between the fourth reference point 214b and the eighth reference point 218b is shorter than the distance D41 between the fourth reference point 214b and the first reference point 211b.

The distance D48 between the fourth reference point 214b and the eighth reference point 218b is shorter than the distance D42 between the fourth reference point 214b and the second reference point 212b.

According to the above-described configuration, the first light-emitting portion 211 and the second light-emitting portion 212 used to calculate the concentration Φo of the oxyhemoglobin can be arranged closer to each other, and the fourth light-emitting portion 214 and the eighth light-emitting portion 218 used to calculate the concentration Φm of the methemoglobin can be arranged closer to each other.

Accordingly, for each of the concentration Φo of the oxyhemoglobin and the concentration Φm of the methemoglobin, an influence of a difference in an optical path length from a plurality of light-emitting portions to the light-detecting portion 22 used for calculation on a change in an absorbance due to pulsation can be reduced. Therefore, it is possible to prevent a decrease in calculation accuracy of the concentration of the light-absorbing substance by pulse photometry.

Figure 9:
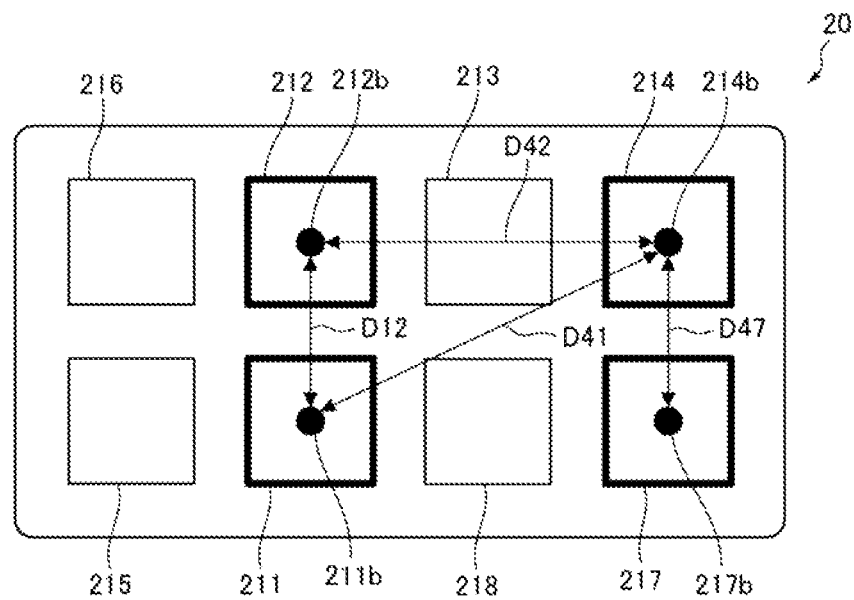
FIG. 9 illustrates another example of the operation of the light-emitting portions of FIG. 2.

As exemplified in FIG. 9, the seventh light-emitting portion 217 can be used to calculate the concentration Φm of the methemoglobin. The seventh wavelength λ7 is determined as a wavelength at which a significant difference appears in the absorbance of the methemoglobin with respect to at least one of the fourth wavelength λ4 and the eighth wavelength λ8. The seventh wavelength λ7 is an example of the fourth wavelength not used for calculating the concentration of the first light-absorbing substance. The seventh wavelength λ7 is also an example of the fourth wavelength used for calculating the concentration of the second light-absorbing substance.

The seventh light-emitting portion 217 may be used in addition to the fourth light-emitting portion 214 and the eighth light-emitting portion 218, or may be used in place of one of the fourth light-emitting portion 214 and the eighth light-emitting portion 218. In the former case, by using the seventh change amount ΔA7 as an offset term for a calculation result of the ratio between the fourth change amount ΔA4 and the eighth change amount ΔA8, it is possible to prevent an influence of other light-absorbing substances and to improve calculation accuracy of the concentration Φm of the methemoglobin. In the latter case, when the concentration Φm of the methemoglobin cannot be appropriately calculated by the fourth light-emitting portion 214 and the eighth light-emitting portion 218 due to various reasons, it is possible to attempt to calculate the concentration Φm of the methemoglobin by using the seventh light-emitting portion 217 as an alternative light source.

In this example, the first light-emitting portion 211, the second light-emitting portion 212, the fourth light-emitting portion 214, and the seventh light-emitting portion 217 are arranged so as to satisfy the following conditions.

The distance D12 between the first reference point 211b and the second reference point 212b is shorter than the distance D41 between the fourth reference point 214b and the first reference point 211b.

The distance D12 between the first reference point 211b and the second reference point 212b is shorter than the distance D42 between the fourth reference point 214b and the second reference point 212b.

The distance D47 between the fourth reference point 214b and the seventh reference point 217b is shorter than the distance D41 between the fourth reference point 214b and the first reference point 211b.

The distance D47 between the fourth reference point 214b and the seventh reference point 217b is shorter than the distance D42 between the fourth reference point 214b and the second reference point 212b.

According to the above-described configuration, the first light-emitting portion 211 and the second light-emitting portion 212 used to calculate the concentration Φo of the oxyhemoglobin can be arranged closer to each other, and the fourth light-emitting portion 214 and the seventh light-emitting portion 217 used to calculate the concentration Φm of the methemoglobin can be arranged closer to each other.

Accordingly, for each of the concentration Φo of the oxyhemoglobin and the concentration Φm of the methemoglobin, an influence of a difference in an optical path length from a plurality of light-emitting portions to the light-detecting portion 22 used for calculation on a change in an absorbance due to pulsation can be reduced. Therefore, it is possible to prevent a decrease in calculation accuracy of the concentration of the light-absorbing substance by pulse photometry.

Figure 10:
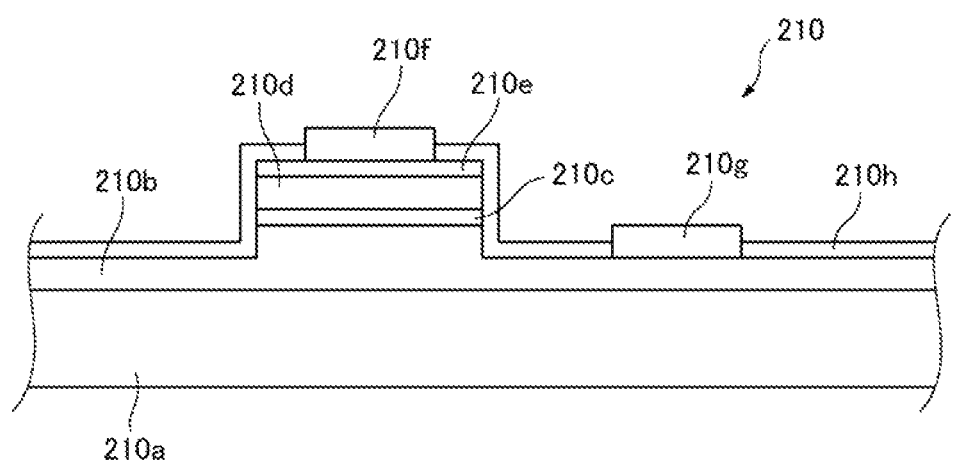
FIG. 10 exemplifies a structure of a light-emitting portion of FIG. 2.

FIG. 10 exemplifies a configuration of a semiconductor light emitter 210 that can be provided in each of the first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, and the eighth light-emitting portion 218.

The semiconductor light emitter 210 can include a substrate 210a, an N-type semiconductor layer 210b, a light-emitting layer 210c, a P-type semiconductor layer 210d, a P-type transparent electrode 210e, a P-side electrode 210f, an N-side electrode 210g, and a protective film 210h.

An upper side in FIG. 10 corresponds to a side adjacent to a light-emitting surface of each light-emitting portion. In a case of this example, in each light-emitting portion provided in the probe 20, the P-type semiconductor layer is disposed on a side adjacent to the light-emitting surface. According to such a configuration, all the light-emitting portions can be efficiently manufactured by a common semiconductor process.

In each light-emitting portion provided in the probe 20, the N-type semiconductor layer may be disposed on the side adjacent to the light-emitting surface.

In the example illustrated in FIG. 10, both the P-side electrode 210f and the N-side electrode 210g are arranged on a side facing the light-emitting surface. However, a configuration in which at least one of the P-side electrode 210f and the N-side electrode 210g is disposed on a side facing the substrate 210a may also be adopted.

Figure 11:
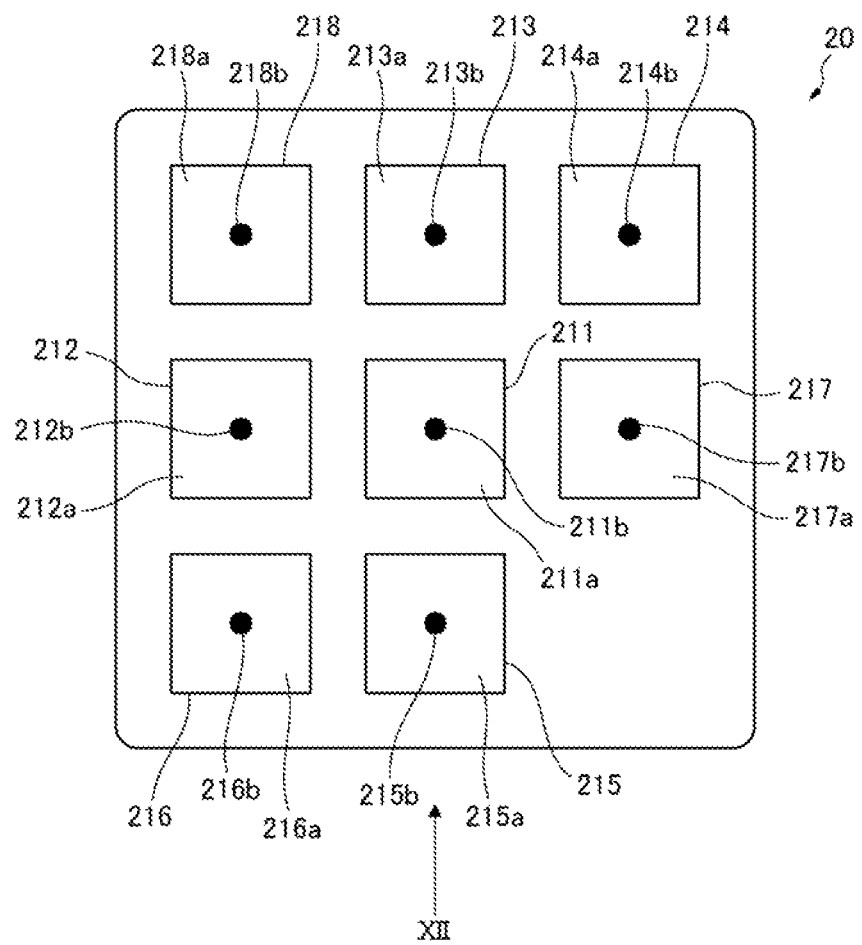
FIG. 11 illustrates another example of the configuration of the light-emitting portions in the probe of FIG. 1.
Figure 12:
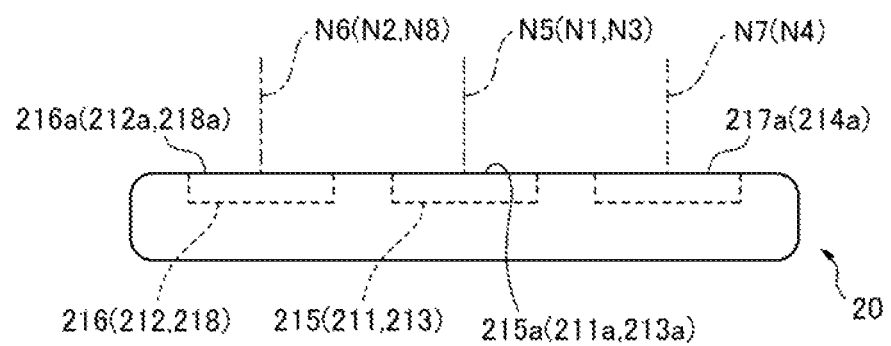
FIG. 12 illustrates another example of the configuration of the light-emitting portions in the probe of FIG. 1.

FIG. 11 illustrates another example of the arrangement of the first light-emitting portion 211, the second light-emitting portion 212, the third light-emitting portion 213, the fourth light-emitting portion 214, the fifth light-emitting portion 215, the sixth light-emitting portion 216, the seventh light-emitting portion 217, and the eighth light-emitting portion 218 of the probe 20. FIG. 12 exemplifies an appearance of a part of the probe 20 when viewed from a direction of an arrow XII in FIG. 11. Substantially the same components as those in the example shown in FIGS. 2 and 3 are denoted by the same reference numerals, and repeated description thereof will be omitted.

Figure 13:
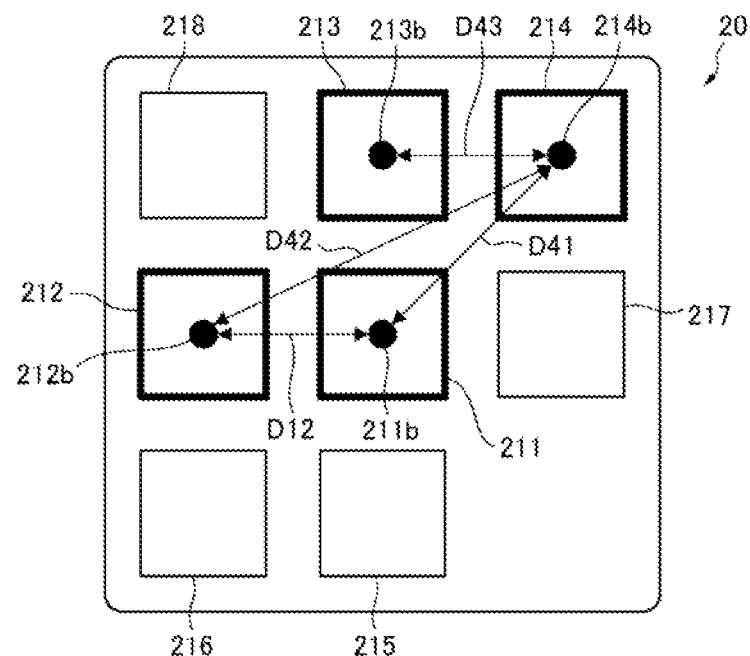
FIG. 13 illustrates an example of an operation of the light-emitting portions of FIG. 11.

FIG. 13 illustrates an example of the operation of the pulse photometry system 10 including the probe 20 configured as exemplified in FIGS. 11 and 12. In this example, the pulse photometer 30 calculates the concentration Φo of the oxyhemoglobin and the concentration Φc of the carboxyhemoglobin. The oxyhemoglobin is an example of the first light-absorbing substance in blood. The carboxyhemoglobin is an example of the second light-absorbing substance in blood.

In this example, in order to calculate the concentration Φo of the oxyhemoglobin, the first light-emitting portion 211 and the second light-emitting portion 212 are used. Since a configuration related to the calculation of the concentration Φo of the oxyhemoglobin is the same as that of the example described with reference to FIG. 4, repeated description will be omitted. The first wavelength λ1 is an example of the first wavelength used for calculating the concentration of the first light absorber. The second wavelength λ2 is an example of the second wavelength used for calculating the concentration of the first light absorber.

In this example, in order to calculate the concentration Φc of the carboxyhemoglobin, the third light-emitting portion 213 and the fourth light-emitting portion 214 are used. Since a configuration related to the calculation of the concentration Φc of the carboxyhemoglobin is the same as that of the example described with reference to FIG. 4, repeated description will be omitted. The fourth wavelength λ4 is an example of the third wavelength not used for calculating the concentration of the first light-absorbing substance. The fourth wavelength λ4 is also an example of the third wavelength used for calculating the concentration of the second light-absorbing substance. The third wavelength λ3 is an example of the fourth wavelength not used for calculating the concentration of the first light-absorbing substance. The third wavelength λ3 is also an example of the fourth wavelength used for calculating the concentration of the second light-absorbing substance.

In this example, the first light-emitting portion 211, the second light-emitting portion 212, the third light-emitting portion 213, and the fourth light-emitting portion 214 are arranged so as to satisfy the following conditions.

The distance D12 between the first reference point 211b and the second reference point 212b is shorter than the distance D41 between the fourth reference point 214b and the first reference point 211b.

The distance D12 between the first reference point 211*b* and the second reference point 212*b* is shorter than the distance D42 between the fourth reference point 214*b* and the second reference point 212*b*.

The distance D43 between the fourth reference point 214*b* and the third reference point 213*b* is shorter than the distance D41 between the fourth reference point 214*b* and the first reference point 211*b*.

The distance D43 between the fourth reference point 214*b* and the third reference point 213*b* is shorter than the distance D42 between the fourth reference point 214*b* and the second reference point 212*b*.

According to the above-described configuration, the first light-emitting portion 211 and the second light-emitting portion 212 used to calculate the concentration Φo of the oxyhemoglobin can be arranged closer to each other, and the third light-emitting portion 213 and the fourth light-emitting portion 214 used to calculate the concentration Φc of the carboxyhemoglobin can be arranged closer to each other.

Accordingly, for each of the concentration Φo of the oxyhemoglobin and the concentration Φc of the carboxyhemoglobin, an influence of a difference in an optical path length from a plurality of light-emitting portions to the light-detecting portion 22 used for calculation on a change in an absorbance due to the pulsation can be reduced. Therefore, it is possible to prevent a decrease in calculation accuracy of the concentration of the light-absorbing substance by pulse photometry.

Figure 14:
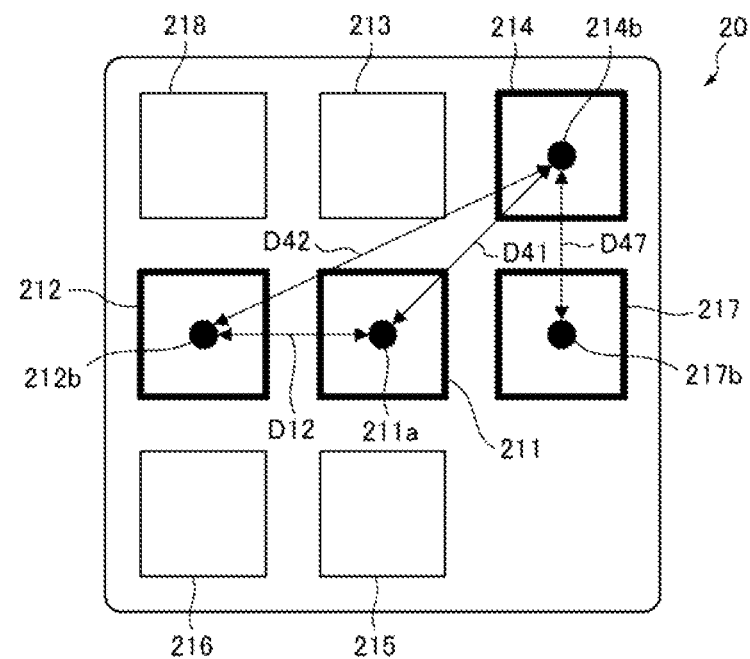
FIG. 14 illustrates another example of the operation of the light-emitting portions of FIG. 11.

As exemplified in FIG. 14, the seventh light-emitting portion 217 can be used to calculate the concentration Φc of the carboxyhemoglobin. Since a configuration related to the calculation of the concentration Φc of the carboxyhemoglobin is the same as that of the example described with reference to FIG. 5, repeated description will be omitted. The seventh wavelength λ7 is an example of the fourth wavelength not used for calculating the concentration of the first light-absorbing substance. The seventh wavelength λ7 is also an example of the fourth wavelength used for calculating the concentration of the second light-absorbing substance.

In this example, the first light-emitting portion 211, the second light-emitting portion 212, the fourth light-emitting portion 214, and the seventh light-emitting portion 217 are arranged so as to satisfy the following conditions.

The distance D12 between the first reference point 211*b* and the second reference point 212*b* is shorter than the distance D41 between the fourth reference point 214*b* and the first reference point 211*b*.

The distance D12 between the first reference point 211*b* and the second reference point 212*b* is shorter than the distance D42 between the fourth reference point 214*b* and the second reference point 212*b*.

The distance D47 between the fourth reference point 214*b* and the seventh reference point 217*b* is shorter than the distance D41 between the fourth reference point 214*b* and the first reference point 211*b*.

The distance D47 between the fourth reference point 214*b* and the seventh reference point 217*b* is shorter than the distance D42 between the fourth reference point 214*b* and the second reference point 212*b*.

According to the above-described configuration, the first light-emitting portion 211 and the second light-emitting portion 212 used to calculate the concentration Φo of the oxyhemoglobin can be arranged closer to each other, and the fourth light-emitting portion 214 and the seventh light-emitting portion 217 used to calculate the concentration Φc of the carboxyhemoglobin can be arranged closer to each other.

Accordingly, for each of the concentration Φo of the oxyhemoglobin and the concentration Φc of the carboxyhemoglobin, an influence of a difference in an optical path length from a plurality of light-emitting portions to the light-detecting portion 22 used for calculation on a change in an absorbance due to the pulsation can be reduced. Therefore, it is possible to prevent a decrease in calculation accuracy of the concentration of the light-absorbing substance by pulse photometry.

Figure 15:
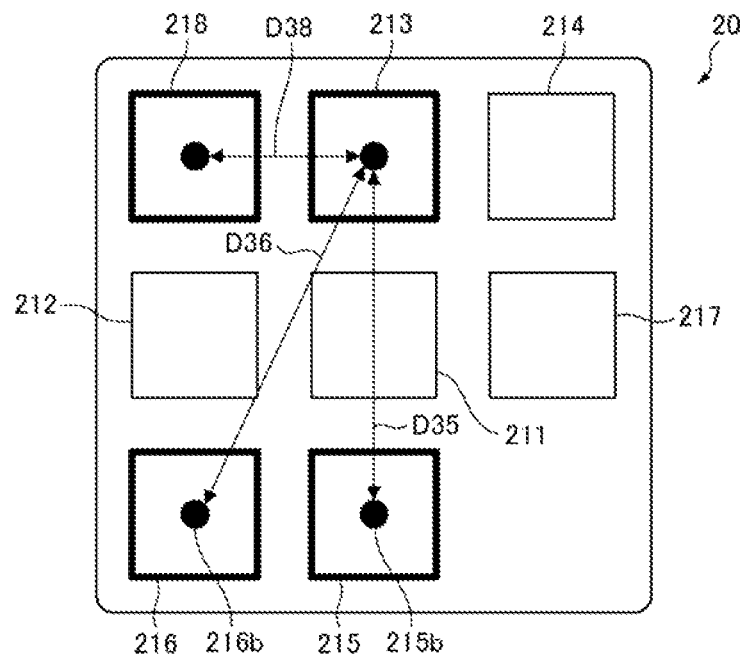
FIG. 15 illustrates another example of the operation of the light-emitting portions of FIG. 11.

FIG. 15 illustrates another example of the operation of the pulse photometry system 10 including the probe 20 configured as exemplified in FIGS. 11 and 12. In this example, the pulse photometer 30 calculates the concentration Φr of the deoxyhemoglobin. The deoxyhemoglobin is an example of the first light-absorbing substance in blood.

In this example, in order to calculate the concentration Φr of the deoxyhemoglobin, the third light-emitting portion 213 and the eighth light-emitting portion 218 are used. The deoxyhemoglobin has wavelength dependence on an absorbance. Since a configuration related to the calculation of the concentration Φr of the deoxyhemoglobin is the same as that of the example described with reference to FIG. 6, repeated description will be omitted. The third wavelength λ3 is an example of the first wavelength used for calculating the concentration of the first light absorber. The eighth wavelength λ8 is an example of the second wavelength used for calculating the concentration of the first light absorber.

In this example, at least one of the fifth light-emitting portion 215 and the sixth light-emitting portion 216 is used to determine an attachment state of the probe 20 to the body 40 of the patient. Since a configuration related to determination of the attachment state is the same as that of the example described with reference to FIG. 6, repeated description will be omitted. Each of the fifth wavelength λ5 and the sixth wavelength λ6 is an example of the third wavelength not used for calculating the concentration of the first light-absorbing substance.

In this example, the fifth light-emitting portion 215, the sixth light-emitting portion 216, the third light-emitting portion 213, and the eighth light-emitting portion 218 are arranged so as to satisfy the following conditions.

The distance D38 between the third reference point 213*b* and the eighth reference point 218*b* is shorter than the distance D35 between the third reference point 213*b* and the fifth reference point 215*b*.

The distance D38 between the third reference point 213*b* and the eighth reference point 218*b* is shorter than the distance D36 between the third reference point 213*b* and the sixth reference point 216*b*.

According to the above-described configuration, an influence of light emitted from a light-emitting portion not used for calculating the concentration Φr of the deoxyhemoglobin on a light-emitting portion used for calculating the concentration Φr of the deoxyhemoglobin can also be reduced. Therefore, it is possible to prevent a decrease in calculation accuracy of the concentration of the light-absorbing substance by pulse photometry.

Figure 16:
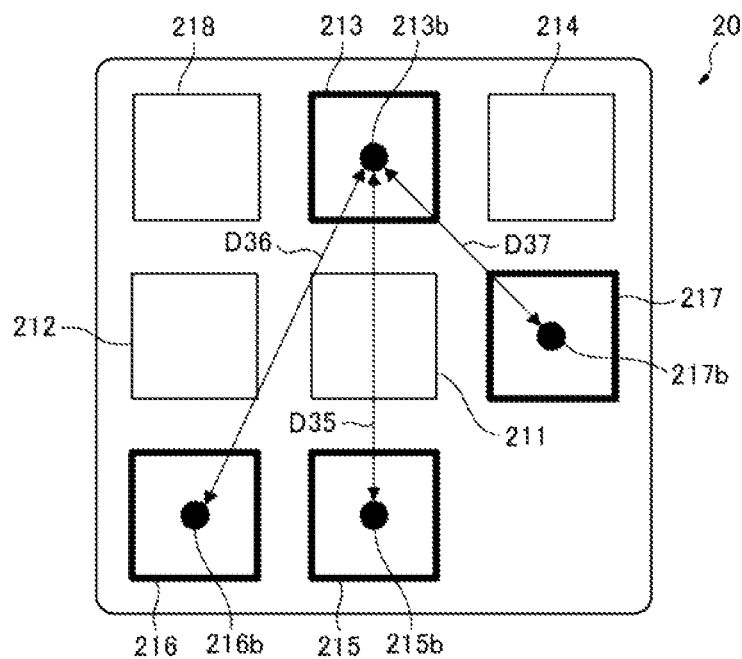
FIG. 16 illustrates another example of the operation of the light-emitting portions of FIG. 11.

As exemplified in FIG. 16, the seventh light-emitting portion 217 can be used to calculate the concentration Φr of the deoxyhemoglobin. Since a configuration related to the calculation of the concentration Φr of the deoxyhemoglobin is the same as that of the example described with reference to FIG. 7, repeated description will be omitted. The seventh wavelength λ7 is an example of the second wavelength used for calculating the concentration of the first light absorber.

In this example, the fifth light-emitting portion 215, the sixth light-emitting portion 216, the third light-emitting portion 213, and the seventh light-emitting portion 217 are arranged so as to satisfy the following conditions.

The distance D37 between the third reference point 213b and the seventh reference point 217b is shorter than the distance D35 between the third reference point 213b and the fifth reference point 215b.

The distance D37 between the third reference point 213b and the seventh reference point 217b is shorter than the distance D36 between the third reference point 213b and the sixth reference point 216b.

According to the above-described configuration as well, an influence of light emitted from a light-emitting portion not used for calculating the concentration Φr of the deoxyhemoglobin on a light-emitting portion used for calculating the concentration Φr of the deoxyhemoglobin can also be reduced. Therefore, it is possible to prevent a decrease in calculation accuracy of the concentration of the light-absorbing substance by pulse photometry.

Figure 17:
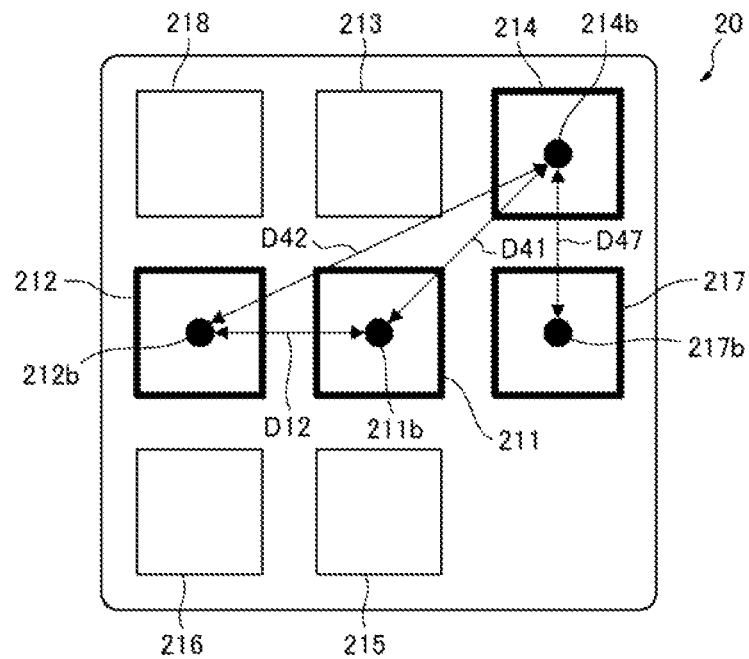
FIG. 17 illustrates another example of the operation of the light-emitting portions of FIG. 11.

FIG. 17 illustrates another example of the operation of the pulse photometry system 10 including the probe 20 configured as exemplified in FIGS. 11 and 12. In this example, the pulse photometer 30 calculates the concentration Φo of the oxyhemoglobin and the concentration Φm of the methemoglobin. The oxyhemoglobin is an example of the first light-absorbing substance in blood. The methemoglobin is an example of the second light-absorbing substance in blood.

In this example, in order to calculate the concentration Φo of the oxyhemoglobin, the first light-emitting portion 211 and the second light-emitting portion 212 are used. Since a configuration related to the calculation of the concentration Φo of the oxyhemoglobin is the same as that of the example described with reference to FIGS. 4 and 5, repeated description will be omitted.

In this example, in order to calculate the concentration Φm of the methemoglobin, the fourth light-emitting portion 214 and the seventh light-emitting portion 217 are used. Since a configuration related to the calculation of the concentration Φm of the methemoglobin is the same as that of the example described with reference to FIG. 9, repeated description will be omitted. The fourth wavelength λ4 is an example of the third wavelength not used for calculating the concentration of the first light-absorbing substance. The fourth wavelength λ4 is also an example of the third wavelength used for calculating the concentration of the second light-absorbing substance. The seventh wavelength λ7 is an example of the fourth wavelength not used for calculating the concentration of the first light-absorbing substance. The seventh wavelength λ7 is also an example of the fourth wavelength used for calculating the concentration of the second light-absorbing substance.

In this example, the first light-emitting portion 211, the second light-emitting portion 212, the fourth light-emitting portion 214, and the seventh light-emitting portion 217 are arranged so as to satisfy the following conditions.

The distance D12 between the first reference point 211b and the second reference point 212b is shorter than the distance D41 between the fourth reference point 214b and the first reference point 211b.

The distance D12 between the first reference point 211b and the second reference point 212b is shorter than the distance D42 between the fourth reference point 214b and the second reference point 212b.

The distance D47 between the fourth reference point 214b and the seventh reference point 217b is shorter than the distance D41 between the fourth reference point 214b and the first reference point 211b.

The distance D47 between the fourth reference point 214b and the seventh reference point 217b is shorter than the distance D42 between the fourth reference point 214b and the second reference point 212b.

According to the above-described configuration, the first light-emitting portion 211 and the second light-emitting portion 212 used to calculate the concentration Φo of the oxyhemoglobin can be arranged closer to each other, and the fourth light-emitting portion 214 and the seventh light-emitting portion 217 used to calculate the concentration Φm of the methemoglobin can be arranged closer to each other.

Accordingly, for each of the concentration Φo of the oxyhemoglobin and the concentration Φm of the methemoglobin, an influence of a difference in an optical path length from a plurality of light-emitting portions to the light-detecting portion 22 used for calculation on a change in an absorbance due to pulsation can be reduced. Therefore, it is possible to prevent a decrease in calculation accuracy of the concentration of the light-absorbing substance by pulse photometry.

Figure 18:
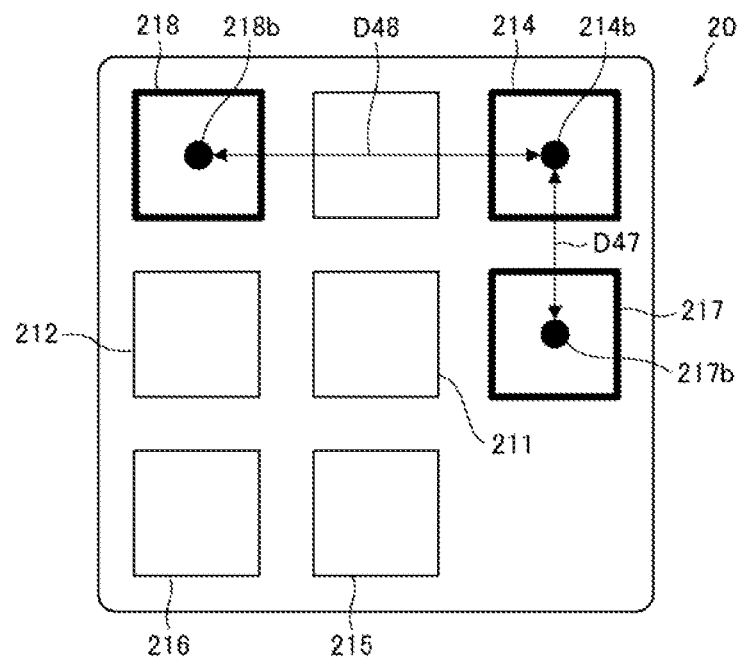
FIG. 18 illustrates another example of the operation of the light-emitting portions of FIG. 11.

FIG. 18 illustrates another example of the operation of the pulse photometry system 10 including the probe 20 configured as exemplified in FIGS. 11 and 12. In this example, the pulse photometer 30 calculates the concentration Φc of the carboxyhemoglobin and the concentration Φm of the methemoglobin. The carboxyhemoglobin is an example of the first light-absorbing substance in blood. The methemoglobin is an example of the second light-absorbing substance in blood.

In this example, in order to calculate the concentration Φc of the carboxyhemoglobin, the fourth light-emitting portion 214 and the seventh light-emitting portion 217 are used. Since a configuration related to the calculation of the concentration Φc of the carboxyhemoglobin is the same as that of the example described with reference to FIG. 5, repeated description will be omitted. The fourth wavelength λ4 is an example of the first wavelength used for calculating the concentration of the first light-absorbing substance. The seventh wavelength λ7 is an example of the second wavelength used for calculating the concentration of the first light-absorbing substance.

In this example, in order to calculate the concentration Φm of the methemoglobin, the fourth light-emitting portion 214 and the eighth light-emitting portion 218 are used. Since a configuration related to the calculation of the concentration Φm of the methemoglobin is the same as that of the example described with reference to FIG. 8, repeated description will be omitted. The eighth wavelength λ8 is an example of the third wavelength not used for calculating the concentration of the first light-absorbing substance.

In this example, the fourth light-emitting portion 214, the seventh light-emitting portion 217, and the eighth light-emitting portion 218 are arranged so as to satisfy the following conditions.

The distance D47 between the fourth reference point 214b and the seventh reference point 217b is shorter than the distance D48 between the fourth reference point 214b and the eighth reference point 218b.

The third light-emitting portion 213 may be used instead of the eighth light-emitting portion 218. In this case, the third light-emitting portion 213, the fourth light-emitting portion 214, and the seventh light-emitting portion 217 are arranged so as to satisfy the following conditions.

The distance D47 between the fourth reference point 214b and the seventh reference point 217b is shorter than the distance D37 between the third reference point 213b and the seventh reference point 217b.

For example, a case where importance related to the calculation of the concentration Φc of the carboxyhemoglobin is higher than importance related to the calculation of the concentration Φm of the methemoglobin will be considered. According to the above-described configuration, regarding the concentration Φc of the carboxyhemoglobin, an influence of a difference in an optical path length from the plurality of light-emitting portions to the light-detecting portion 22 used for the calculation on a change in an absorbance due to the pulsation can be reduced. That is, when some of the plurality of light-emitting portions are used in combination with the calculation of a plurality of concentrations of light absorbers, it is possible to prevent a decrease in calculation accuracy of a concentration of a light absorber having relatively high importance.

The above embodiment is merely an example for facilitating the understanding of the presently disclosed subject matter. The configuration according to the above embodiment can be appropriately changed or improved without departing from the spirit of the presently disclosed subject matter.

The pulse photometry system 10 may include three or more optional number of light-emitting portions in accordance with the number and type of the plurality of light-absorbing substances for which concentration calculation is required. Examples of other light-absorbing substances may also include bilirubin and glucose.

The light-absorbing substance to be subjected to concentration calculation may include not only a substance generated in the body of the patient, but also pigment injected into a blood vessel for the purpose of cardiac output measurement, liver function measurement, or a contrast examination using indocyanine green (ICG), for example.

In the above embodiment, the plurality of light-emitting portions are arranged at equal intervals. However, an interval between the adjacent light-emitting portions may be appropriately determined in accordance with the number and the type of the light-absorbing substances for which the concentration calculation is required.

The pulse photometer 30 may be provided as an independent device, or may be implemented as a device that provides a function of calculating a concentration of a light-absorbing substance in a patient monitor that acquires a plurality of types of physiological parameters.

What is claimed is:

1. A probe configured to be connected to a pulse photometer, the probe comprising:
   a first light-emitting portion having a first light-emitting surface from which only first light having a first wavelength is emitted, the first wavelength being used for calculating a concentration of a first light-absorbing substance in blood of a patient;
   a second light-emitting portion having a second light-emitting surface from which only second light having a second wavelength that is different from the first wavelength is emitted, the second wavelength being used for calculating the concentration of the first light-absorbing substance;
   a third light-emitting portion having a third light-emitting surface from which only third light having a third wavelength that is different from the first wavelength and the second wavelength is emitted, the third wavelength being not used for calculating the concentration of the first light-absorbing substance, and
   a fourth light-emitting portion having a fourth light-emitting surface from which fourth light having a fourth wavelength that is different from the first wavelength, the second wavelength, and the third wavelength is emitted, the fourth wavelength being not used for calculating the concentration of the first light-absorbing substance,
   wherein a distance between a first reference point of the first light-emitting portion when viewed from a normal line direction of the first light-emitting surface and a second reference point of the second light-emitting portion when viewed from a normal line direction of the second light-emitting surface is shorter than a distance between a third reference point of the third light-emitting portion when viewed from a normal line direction of the third light-emitting surface and the first reference point,
   wherein the distance between the first reference point and the second reference point is shorter than a distance between the third reference point and the second reference point, and
   wherein a distance between a fourth reference point of the fourth light-emitting portion when viewed from a normal line direction of the fourth light-emitting surface and the third reference point is shorter than a distance between the first reference point or the second reference point and the third reference point.

2. The probe according to claim 1, wherein the third light is used for calculating a concentration of a second light-absorbing substance in blood of the patient, the concentration of the second light-absorbing substance being different from the concentration of the first light-absorbing substance.

3. The probe according to claim 2, wherein the concentration of the first light-absorbing substance and the concentration of the second light-absorbing substance are two of a concentration of oxyhemoglobin, a concentration of deoxyhemoglobin, a concentration of carboxyhemoglobin, and a concentration of methemoglobin.

4. The probe according to claim 1, wherein the first light-emitting portion, the second light-emitting portion, and the third light-emitting portion include respective semiconductor light-emitting portions having respective semiconductor layers, the respective semiconductor layers being the same type and being arranged adjacent to the first light-emitting surface, the second light-emitting surface, and the third light-emitting surface.

5. The probe according to claim 1, wherein the third light and the fourth light are used for calculating a concentration of a second light-absorbing substance in blood of the patient, the concentration of the second light-absorbing substance being different from the concentration of the first light-absorbing substance.

6. The probe according to claim 5, wherein the concentration of the first light-absorbing substance and the concentration of the second light-absorbing substance are two of a concentration of oxyhemoglobin, a concentration of deoxyhemoglobin, a concentration of carboxyhemoglobin, and a concentration of methemoglobin.

7. The probe according to claim 1, wherein the first light-emitting portion, the second light-emitting portion, the third light-emitting portion, and the fourth light-emitting portion include respective semiconductor light-emitting portions having respective semiconductor layers, the respective semiconductor layers being the same type and being arranged adjacent to the first light-emitting surface, the second light-emitting surface, the third light-emitting surface, and the fourth light-emitting surface.

8. A pulse photometry system comprising:
- a first light-emitting portion having a first light-emitting surface from which only first light having a first wavelength is emitted;
- a second light-emitting portion having a second light-emitting surface from which only second light having a second wavelength that is different from the first wavelength is emitted;
- a third light-emitting portion having a third light-emitting surface from which only third light having a third wavelength that is different from the first wavelength and the second wavelength is emitted;
- a fourth light-emitting portion having a fourth light-emitting surface from which fourth light having a fourth wavelength that is different from the first wavelength, the second wavelength, and the third wavelength is emitted,
- a light-detecting portion configured to output a first signal corresponding to an intensity of the first light that has passed through a tissue of a patient, a second signal corresponding to an intensity of the second light that has passed through the tissue, a third signal corresponding to an intensity of the third light that has passed through the tissue, and a fourth signal corresponding to an intensity of the fourth light that has passed through the tissue; and
- a processor configured to calculate a concentration of a first light-absorbing substance in blood of the patient based on the first signal and the second signal and not based on the third signal and the fourth signal, wherein a distance between a first reference point of the first light-emitting portion when viewed from a normal line direction of the first light-emitting surface and a second reference point of the second light-emitting portion when viewed from a normal line direction of the second light-emitting surface is shorter than a distance between a third reference point of the third light-emitting portion when viewed from a normal line direction of the third light-emitting surface and the first reference point, and wherein the distance between the first reference point and the second reference point is shorter than a distance between the third reference point and the second reference point, wherein a distance between a fourth reference point of the fourth light-emitting portion when viewed from a normal line direction of the fourth light-emitting surface and the third reference point is shorter than a distance between the first reference point or the second reference point and the third reference point.

\* \* \* \* \*